US009744217B2

(12) United States Patent
Otagiri et al.

(10) Patent No.: US 9,744,217 B2
(45) Date of Patent: Aug. 29, 2017

(54) BILIRUBIN EXCRETION ENHANCER (71) Applicant: Nipro Corporation, Osaka (JP)

(72) Inventors: Masaki Otagiri, Kumamoto (JP); Toru Maruyama, Kumamoto (JP); Yu Ishima, Kumamoto (JP); Ai Minomo, Kumamoto (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 14/877,228

(22) Filed: Oct. 7, 2015

(65) Prior Publication Data

US 2016/0058844 A1  Mar. 3, 2016

Related U.S. Application Data (63) Continuation of application No. 14/237,694, filed as application No. PCT/JP2012/070310 on Aug. 9, 2012, now abandoned.

(30) Foreign Application Priority Data

Aug. 10, 2011  (JP) ................. 2011-175403

(51) Int. Cl.
*A61K 38/38* (2006.01)
*C07K 14/765* (2006.01)
*A61K 38/00* (2006.01)

(52) U.S. Cl.
CPC .......... *A61K 38/385* (2013.01); *C07K 14/765* (2013.01); *A61K 38/00* (2013.01)

(58) Field of Classification Search
None
See application file for complete search history.

(56) References Cited

U.S. PATENT DOCUMENTS

| 5,380,712 A * | 1/1995 | Ballance .............. C07K 14/765 435/69.6 |
| 5,780,594 A | 7/1998 | Carter |
| 2005/0256303 A1 | 11/2005 | Otagiri et al. |
| 2007/0041987 A1 | 2/2007 | Carter et al. |
| 2011/0020865 A1 | 1/2011 | Payne et al. |
| 2013/0196924 A1* | 8/2013 | Bucci ................. G01N 33/6896 514/17.7 |
| 2014/0147874 A1* | 5/2014 | Cotter et al. ................ 435/18 |

FOREIGN PATENT DOCUMENTS

| EP | 322094 | * | 6/1989 |
| EP | 0322094 A1 | | 6/1989 |
| JP | 2005245268 A | | 9/2005 |
| JP | 2008543323 A | | 12/2008 |
| JP | 2010172277 A | | 8/2010 |
| WO | 2010/061283 | * | 6/2010 |

OTHER PUBLICATIONS

2014 Interim Guidance on Patent Subject Matter Eligibility (79 FR 74618), which is found at: http://www.uspto.gov/patents/law/exam/interim-guidance-subject-matter-eligibility.jsp.*
Ahmad et al., "Intermediate formation at lower urea concentration in 'B' isomer of human serum albumin: a case study using domain specific ligands", Biochemical and Biophysical Research Communications, 2004, p. 166-173, vol. 314.
Dockal et al., "The Three Recombinant Domains of Human Serum Albumin", The Journal of Biological Chemistry, 1999, p. 29303-29310, vol. 274, No. 41.
Minomo et al., "Biological characteristics of two lysines on human serum albumin in the highaffinity binding of 4Z, 15z-bilirubin-IXalpha revealed by phage display", FEBS Journal, 2011, p. 4100-4111, entire text, particularly, p. 1109, left column, 2nd paragraph, vol. 278, No. 21.
Nishimura et al., "Bilirubin Nyochu Haisetsu Sa yo 0 Sokushin shita Hi to Kessei Albumin Domain II Hen'itai ni yoru Teishinshusei Ketsueki Joka Ryoho no Kaihatsu", Clinical Pharmacy Symposium, Jul. 2012, p. 218, entire text, vol. 20.
Otagiri, et al., "Hi to Kessei Albumin Domain II ni yoru Bilirubin Nyochu Haisetsu Sokushin Sayo", Annual Meeting of the Japan Society of Drug Delivery System Program Yokoshu, Jun. 2012, p. 154, entire text, vol. 28.
Otagiri, et al., "Hilo Kessei Albumin Domain II ni yoru Bilirubin Nyochu Haisetsu Sokushin Sayo", Abstracts of Annual Meeting of Pharmaceutical Society of Japan, Mar. 2012, p. 209, entire text, vol. 132, No. 4.
Petersen et al., "A Dynamic Model for Bilirubin Binding to Human Serum Albumin", The Journal of Biological chemistry, 2000, pp. 20985-20995, vol. 275, No. 28.
Vedrova, "The influence of human albumin on hyperbiliaubin in the newborn", Acta Fag.Med. Univ. Brun., 1965, p. 47-57, entire text, particularly, p. 55, Summary, vol. 21, No. 47.
Zunszain et al., "Crystallographic Analysis of Human Serum Albumin Complexed with 4Z, 15E-Bilirubin-1Xalpha", Journal of Molecular Biology, 2008, p. 394-406, entire text, particularly, p. 396, left column, the last paragraph to right column, 1st paragraph, p. 401, left column, 2nd paragraph to p. 403, right column, 1st paragraph, vol. 381, No. 2.

* cited by examiner

Primary Examiner — Maury Audet
(74) Attorney, Agent, or Firm — The Webb Law Firm (57) ABSTRACT The purpose of the present invention is to establish a novel therapy method for hyperbilirubinemia and therefore, to provide a bilirubin excretion enhancer. The present invention provides a bilirubin excretion enhancer comprising, as an active ingredient, a serum albumin domain II-like protein comprising a serum albumin subdomain IIA. In one embodiment, the serum albumin subdomain IIA has an amino acid sequence of SEQ ID NO: 1. in one embodiment, the serum albumin domain II-like protein is a serum albumin domain II. In one embodiment, the serum albumin domain II comprises the amino acid sequence of SEQ ID NO: 4.

3 Claims, 4 Drawing Sheets

BILIRUBIN EXCRETION ENHANCER

CROSS-REFERENCE TO RELATED APPLICATIONS

This application is a continuation of U.S. patent application Ser. No. 14/237,694, filed Aug. 9, 2012, which is the United States national phase of International Application No. PCT/JP2012/070310 filed Aug. 9, 2012, and claims priority to Japanese Patent Application No. 2011-175403 filed Aug. 10, 2011, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is SequenceListing.txt. The size of the text file is 17,419 bytes and the text file was created on Jan. 28, 2014.

BACKGROUND OF THE INVENTION

Field of the Invention

The present invention relates to a bilirubin excretion enhancer. More specifically, the present invention relates to a bilirubin excretion enhancer with a serum albumin domain II-like protein, containing the subdomain IIA of serum albumin, as an active ingredient.

Description of Related Art

Figure 1:
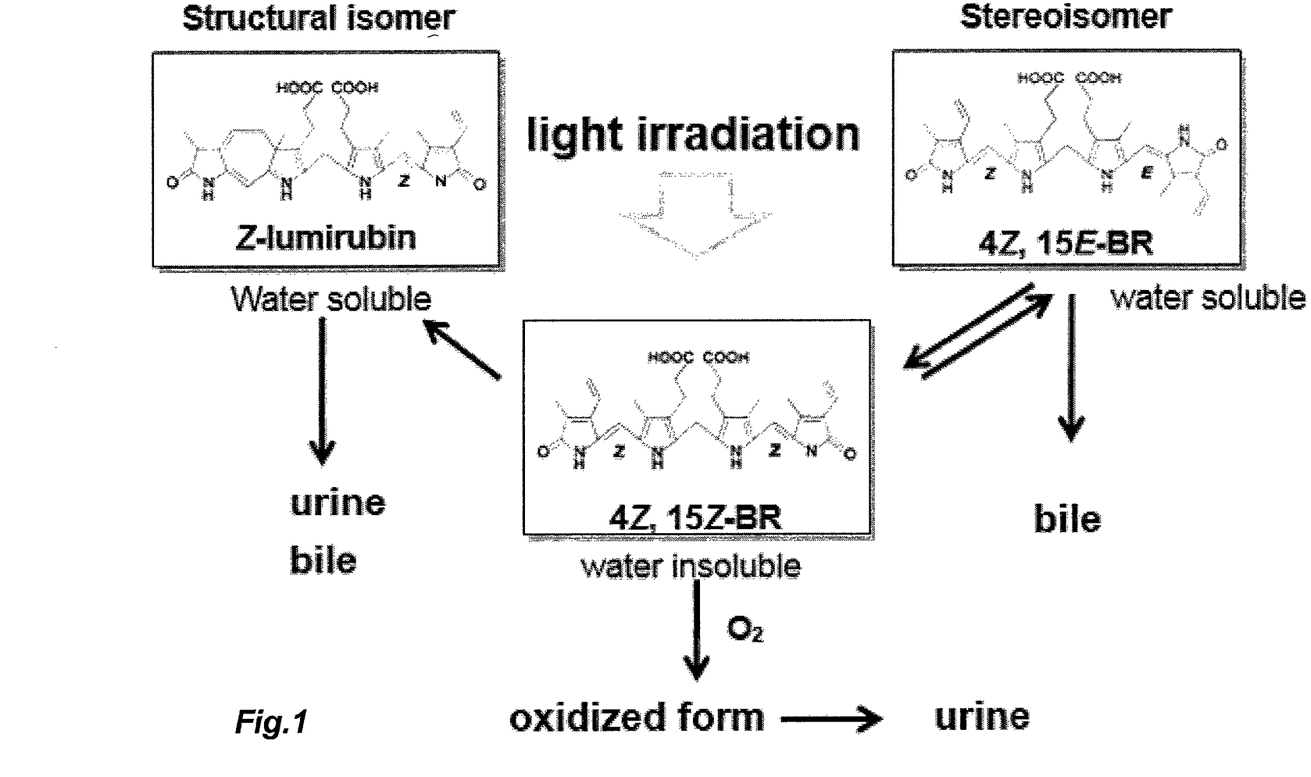
FIG. 1 shows the mechanism for bilirubin phototherapy.

Bilirubin is a final product of the degradation of a heme which is a component of a red blood cell. Within various isomers thereof, the isomer that exists most abundantly in the body is 4Z, 15Z-bilirubin-IXα (hereinafter, referred to as 4Z, 15Z-BR). A newborn is susceptible to hyperbilirubinemia and jaundice because of the immaturity of liver, which is a 4Z, 15Z-BR metabolizing tissue. If the level of bilirubin becomes high, bilirubin may deposit on cranial nerves, thereby causing encephalopathy. Nowadays, the first-line therapy for jaundice of the newborn is phototherapy. Phototherapy is a therapy in which the skin of a newborn is irradiated with light to convert 4Z, 15Z-BR having a low water solubility to an isomer having a high water solubility such as 4Z, 15E-bilirubin-IXα (4Z, 15E-BR) or Z-lumirubin, and promote the excretion of bilirubin into urine and bile. The mechanism for bilirubin phototherapy is shown in FIG. 1. However, although phototherapy is effective for bilirubin deposited on the skin, it is not effective for bilirubin in blood because light does not reach bilirubin in blood. Moreover, since the skin of an adult hardly transmits light, phototherapy is performed only on a newborn.

Therefore, at this time, plasma exchange in which plasma in blood is exchanged to lower the bilirubin concentration or adsorption removal of bilirubin using a column for bilirubin adsorption is performed. However, the adsorption removal method involves an increased risk of infectious diseases, and removes proteins and vitamins useful for a living body.

Human serum albumin (hereinafter, referred to as HSA) is the main protein present in adult serum, is produced in the liver, and functions as a carrier transporting various serum molecules. Moreover, bilirubin binds to HSA and is carried to the liver, and then binds to glucuronic acid in the liver to become a conjugated bilirubin that dissolves in water more easily. This conjugated bilirubin is secreted from the liver as bile.

HSA is a single-stranded protein (SEQ ID NO: 10) of 585 amino acids, and the basic structure is composed of three domains (domain I, II and III) having a high homology, each of which is segmented into subdomains (A and B). The domain I ranges amino acid positions 1 to 197, the domain II ranges amino acid positions 187 to 385, and the domain III ranges amino acid positions 381 to 585.

It is reported that the site I (domain II) is a high affinity binding site for bilirubin. The inventors have obtained an albumin variant having a high binding activity with respect to bilirubin, and found that the amino acids at positions 195 and 199 contribute to bilirubin binding (Patent Document 1). Moreover, the inventors have produced a protein including the domain I of HSA by genetic recombination (Patent Document 2).

PRIOR ART DOCUMENTS

Patent Documents

Patent Document 1: Japanese Laid-Open Patent Publication No. 2010-172277
Patent Document 2: Japanese Laid-Open Patent Publication No. 2005-245268

SUMMARY OF THE INVENTION

Problems to be Solved by the Invention

It is an object of the present invention to provide a bilirubin excretion enhancer in order to establish a novel therapeutic method for hyperbilirubinemia.

Means for Solving the Problems

The inventors have intensively studied a method for direct excretion of bilirubin, particularly 4Z,15Z-BR in order to solve the above problems, and found that a serum albumin domain II-like protein including the subdomain IIA of serum albumin binds to bilirubin and the bound bilirubin is excreted to urine. Thus the present invention was accomplished.

The present invention provides a bilirubin excretion enhancer comprising, as an active ingredient, a serum albumin domain II-like protein comprising a serum albumin subdomain IIA.

In one embodiment, the serum albumin subdomain IIA has an amino acid sequence of SEQ ID NO: 1.

In one embodiment, the serum albumin domain II-like protein is a serum albumin domain II.

In one embodiment, the serum albumin domain II has an amino acid sequence of SEQ ID NO: 4.

In one embodiment, the serum albumin domain II-like protein comprises a serum albumin subdomain IB.

In one embodiment, the bilirubin excretion enhancer is a urinary excretion enhancer.

In one embodiment, the bilirubin excretion enhancer is a 4Z, 15Z-bilirubin-IXα excretion enhancer.

Effects of Invention

A serum albumin domain II-like protein as the active ingredient of the bilirubin excretion enhancer of the present invention can bind to bilirubin to allow for rapidly excreting bilirubin into urine. Particularly, it can bind to 4Z, 15Z-BR that has poor water solubility and is not normally excreted into urine, thereby enhancing the renal excretion. Accordingly, it is effective as a bilirubin excretion enhancer and a therapeutic agent of hyperbilirubinemia. Moreover, it can be safely administered to a newborn as well as to an adult, since HSA is present in the body and has excellent safety.

DESCRIPTION OF THE INVENTION

A serum albumin subdomain IIA in the present invention refers to a region constituting the subdomain A of the domain II of serum albumin, and a serum albumin fragment of that region.

In the present invention, serum albumin is albumin contained in serum, and may be derived from, for example, humans or other warm-blooded animals (e.g., cattle, monkeys, pigs, horses, sheep, goats, dogs, cats, rabbits, mice, rats, hamsters, guinea pigs, chickens, and quails). In view of the application to pharmaceutical drugs, human serum albumin is preferable.

Wild type human serum albumin (hereinafter, referred to as HSA) has a molecular weight of 66.5 kDa, and the amino acid sequence from positions 1 to 585t of SEQ ID NO: 10 in Sequence Listing. Serum albumin of the present invention includes genetic polymorphisms of HSA and mutants thereof. Up to now, 60 or more types of genetic polymorphisms of HSA are reported. The variant here refers to HSA whose one or more amino acids are deleted, substituted or added.

The serum albumin subdomain IIA of the present invention includes the subdomain IIA of serum albumin, genetic polymorphisms thereof, and mutants thereof. Preferably, it is the subdomain IIA of HSA (hereinafter, referred to as HSA subdomain IIA). The serum albumin subdomain IIA contains a bilirubin binding site.

The HSA subdomain IIA has at least the amino acid sequence of SEQ ID NO: 1 (positions 187 to 248 of SEQ ID NO: 10). More preferably, it has the amino acid sequence of SEQ ID NO: 2 (positions 187 to 295 of SEQ ID NO: 10). Even more preferably, it has the amino acid sequence of SEQ ID NO: 3 (positions 187 to 298 of SEQ ID NO: 10).

The HSA subdomain IIA includes genetic polymorphisms of the HSA subdomain IIA and mutants thereof. The mutant here refers to an HSA subdomain IIA whose one or more amino acids are deleted, substituted or added, and is not limited as long as it has an affinity to bilirubin. Preferably 1 to 20 amino acids, more preferably 1 to 10 amino acids, and even more preferably 1 to 5 amino acids are deleted, substituted or added. Preferable examples of an HSA subdomain IIA mutant include F211R/R218L and F211/R218S/R222W. F211R/R218L is an HSA subdomain IIA mutant in which phenylalanine at the position 211 is substituted with arginine and arginine at the position 218 is substituted with leucine, and F211/R218S/R222W is an HSA subdomain IIA mutant in which phenylalanine at the position 211 is substituted with leucine, arginine at the position 218 is substituted with serine and arginine at the position 222 is substituted with tryptophan.

The HSA subdomain IIA includes proteins having an amino acid sequence different from but substantially identical to that of the subdomain IIA of HSA having the amino acid sequence of Sequence ID No: 1, 2 or 3, and having an affinity to bilirubin equivalent to or more than that of the subdomain IIA of HSA having the amino acid sequence of SEQ ID NO: 1, 2 or 3 so that it can bind to bilirubin to allow for facilitating renal excretion.

In the present invention, the amino acid sequence that is substantially identical to that of the subdomain IIA of HSA having the amino acid sequence of SEQ ID NO: 1, 2 or 3 refers to an amino acid sequence that has preferably approximately 80% or more, more preferably approximately 90% or more, and even more preferably approximately 95% or more homology to the subdomain IIA of HSA having the amino acid sequence of SEQ ID NO: 1, 2 or 3.

Here, "homology" means a ratio (%) of the same amino acid residues and similar amino acid residues to all the overlapping amino acid residues in an optimal alignment of two amino acid sequences determined by using a known mathematical algorithm in the art (preferably, the algorithm may be taken account of the introduction of gaps into one or both of the two sequences for the optimal alignment). "Similar amino acids" refers to amino acids that are similar in physicochemical properties, and examples thereof include amino acids classified into the same group such as aromatic amino acids (Phe, Trp, and Tyr), aliphatic amino acids (Ala, Leu, Ile, and Val), polar amino acids (Gln and Asn), basic amino acid (Lys, Arg, and His), acidic amino acids (Glu and Asp), amino acids having a hydroxyl group (Ser and Thr), or amino acids having a small side chain (Gly, Ala, Ser, Thr, and Met). It is predicted that the substitution with such a similar amino acid does not lead to any change in protein phenotype (i.e., conservative amino acid substitution). Specific examples of conservative amino acid substitution are well known in the art and described in various documents (see, for example, Bowie et al., Science, 247: 1306-1310 (1990)).

A serum albumin domain II-like protein of the present invention is a fragment of serum albumin that contains the serum albumin subdomain IIA, and has a half or less molecular weight of that of serum albumin. Preferably, the molecular weight is one-third or less. A human serum albumin domain II-like protein (hereinafter, referred to as HSA domain II-like protein) is an HSA fragment containing the HSA subdomain IIA, and has a half (33 kDa) or less molecular weight of that of HSA, preferably the molecular weight is one-third (22 kDa) or less.

A serum albumin domain II-like protein of the present invention is a fragment of serum albumin that contains the serum albumin subdomain IIA of the present invention. Preferable serum albumin domain II-like protein is HSA domain II-like protein. HSA domain II-like protein is an HSA fragment containing the HSA subdomain IIA of the present invention. Examples thereof include an HSA fragment composed of the subdomain IIA, an HSA fragment composed of the domain II, an HSA fragment composed of the subdomain IB and the subdomain IIA, an HSA fragment composed of the domain II and the subdomain IB, and an HSA fragment composed of the domain I and the subdomain IIA. Preferably, the serum albumin domain II-like protein of the present invention does not contain the domain III.

The subdomain IIA in serum albumin domain II-like protein may not have the same conformation as that of the subdomain IIA in serum albumin, and may contain any structure in which the subdomain IIA hardly retains the conformation. Also, a region other than the subdomain IIA region of serum albumin domain II-like protein may or may not constitute a domain, and there is no limitation on the positions of the N-terminus and the C-terminus as long as the subdomain IIA region is contained therein.

In one embodiment of a serum albumin domain II-like protein of the present invention, the serum albumin domain IIA is a protein composed of the foregoing serum albumin domain IIA region.

In one embodiment of a serum albumin domain II-like protein of the present invention, the serum albumin domain II includes the domain II of serum albumin, genetic polymorphisms thereof and mutants thereof. Preferably, it is the domain II of HSA (hereinafter, referred to as HSA domain II).

Preferably, the HSA domain II has the amino acid sequence of SEQ ID NO: 4 (positions 187 to 341 of SEQ ID NO: 10). More preferably, it has the amino acid sequence of SEQ ID NO: 5 (positions 187 to 361 of SEQ ID NO: 10). Even more preferably, it has the amino acid sequence of SEQ ID NO: 6 (positions 187 to 385 of SEQ ID NO: 10).

The HSA domain II includes genetic polymorphisms of the HSA domain II and their mutants. The mutant here refers to a HSA domain II whose one or more amino acids are deleted, substituted or added, and is not limited as long as it has the affinity to bilirubin. Preferably 1 to 20 amino acids, more preferably 1 to 10 amino acids, and even more preferably 1 to 5 amino acids are deleted, substituted or added.

The HSA domain II includes a protein that has an amino acid sequence different from but substantially identical to that of the domain II of HSA having the amino acid sequence of SEQ ID NO: 4, 5 or 6, and that has an affinity to bilirubin equivalent to or more than that of the HSA domain II having the amino acid sequence of SEQ ID NO: 4, 5 or 6 so that it can bind to bilirubin to allow for renal excretion.

In the present invention, the amino acid sequence that is substantially identical to that of the domain II of HSA having the amino acid sequence of SEQ ID NO: 4, 5 or 6 refers to an amino acid sequence that has preferably approximately 80% or more, more preferably approximately 90% or more, and even more preferably approximately 95% or more homology to the domain II of HSA having the amino acid sequence of SEQ ID NO: 4, 5 or 6. Homology is as described above.

Serum albumin domain II-like protein of the present invention contains the subdomain IIA region, and may additionally contain the domain I, the subdomain IB or the subdomain IIB. These include genetic polymorphisms thereof and mutants thereof.

In one embodiment of a serum albumin domain II-like protein of the present invention, a protein containing the serum albumin subdomain IB contains the subdomain IB and the subdomain IIA. The protein includes genetic polymorphisms thereof and mutants thereof. Preferably, it is an HSA fragment composed of the HSA domain IB and the HSA subdomain IIA.

Preferably, the HSA fragment composed of the HSA domain IB and the HSA subdomain IIA has the amino acid sequence of SEQ ID NO: 7 (positions 187 to 298 of SEQ ID NO: 10). More preferably, it has the amino acid sequence of SEQ ID NO: 8 (positions 150 to 298 of SEQ ID NO: 10). Even more preferably, it has the amino acid sequence of SEQ ID NO: 9 (positions 124 to 298 of SEQ ID NO: 10).

The HSA fragment composed of the HSA domain IB and the HSA subdomain IIA includes genetic polymorphisms thereof and mutants thereof. The mutant here refers to an HSA fragment composed of the HSA domain IB and the HSA subdomain IIA, whose one or more amino acids are deleted, substituted or added, and is not limited as long as it has the affinity to bilirubin. Preferably 1 to 20 amino acids, more preferably 1 to 10 amino acids, and even more preferably 1 to 5 amino acids are deleted, substituted or added.

The HSA fragment composed of the HSA domain IB and the HSA subdomain IIA includes a protein that has an amino acid sequence different from but substantially identical to that of the HSA fragment having the amino acid sequence of SEQ ID NO: 7, 8 or 9, and that has an affinity to bilirubin equal to or more than that of the HSA fragment having the amino acid sequence of SEQ ID NO: 7, 8 or 9 so that it can bind to bilirubin to allow for renal excretion.

In the present invention, the amino acid sequence that is substantially identical to that of the HSA fragment having the amino acid sequence of SEQ ID NO: 7, 8 or 9 refers to an amino acid sequence that has preferably approximately 80% or more, more preferably approximately 90% or more, and even more preferably approximately 95% or more homology to the HSA fragment having the amino acid sequence of SEQ ID NO: 7, 8 or 9. Homology is as described above.

HSA domain II-like protein as an active ingredient of the bilirubin excretion enhancer of the present invention can be obtained by cleaving HSA obtained from plasma with a reagent such as CNBr and purifying a fragment containing the subdomain IIA. Also, HSA domain II-like protein can be obtained by genetic recombination, for example, by inserting a DNA encoding the protein of interest into an expression vector, is transforming a suitable host with the vector, and culturing the host. For example, HSA domain II-like protein can be produced and purified according to the procedures as described in Japanese Laid-Open Patent Publication Nos. 2010-172277 and 2005-245268.

Bilirubin, of which excretion is enhanced according to the present invention, includes stereoisomers such as 4Z, 15Z-BR and 4Z, 15E-BR, and structural isomers such as Z-lumirubin.

Bilirubin excretion enhancement according to the present invention refers to enhancement of the excretion of bilirubin in the body out of the body to reduce the amount of bilirubin in the body, particularly in blood. Preferably, the excretion of bilirubin into urine is enhanced. More specifically, the conjugate of bilirubin with the HSA domain II-like protein of the present invention is filtered and excreted by the kidney to promote the excretion of bilirubin out of the body.

As the formulation of the bilirubin excretion enhancer of the present invention, tablets, pills, powders, suspensions, capsules, suppositories, injections, ointments, and patches are exemplified. Preferably, it is liquid formulation obtained from purified HSA domain II-like protein or lyophilized formulation obtained by lyophilizing HSA domain II-like protein. A kit formulation may be prepared with lyophilized formulation in combination with dissolving liquid.

A stabilizer such as sugar, sugar alcohol and amino acid, a pH regulator, and a vehicle can be added to the formulation. Also, if necessary, viral inactivating treatment or sterilizing treatment can be performed before or after drug formulation.

There is no limitation on the administration mute of the bilirubin excretion enhancer of the present invention. Examples thereof include transvenous, transarterial, oral, transcutaneous, and transmucosal. The dose and frequency of administration are adjusted while observing the condition of a patient considering the patient's condition, age, sex, body weight, meal, and so on. For example, in the case of injections, a dose of 10-50 mg/bodyweight can be administered once to three times a day. Also, the administration can be once a few days, or only as needed.

Hereinafter, the present invention will be specifically described by way of examples, but the present invention is not limited to the examples.

EXAMPLES

Example 1

HSA donated by The Chemo-Sero-Therapeutic Research Institute was used. Ten milliliters of the solution of CNBr in 70% formic acid solution was added to 30 mg of HSA so that the molar concentration ratio of CNBr to methionine residues in HSA is 200:1, and the mixture was incubated for 24 hours at room temperature in the dark. After that, 40 ml of ion exchanged water was added to the mixture to quench the reaction, and the obtained solution was subjected to centrifugal concentration with Speed vac (registered trademark) plus (Savant Inc.). After buffer was exchange, the sample was purified with HiTrap Blue HP using AKTA Prime plus (GE Healthcare). The column was equilibrated with 20 mM sodium phosphate (pH 7.0), and eluted with gradient of 2 M potassium thiocyanate+20 mM sodium phosphate (pH 7.0). Fractions in which 20 kDa protein was eluted were confirmed by SDS-PAGE, and subjected to the following experiment.

The obtained protein of 20 kDa was confirmed to be HSA domain II-like protein (SEQ ID NO: 9 (Cys124-Met298 of SEQ ID NO: 10)) composed of the domains IB and IIA by non-reducing SDS-PAGE. The resultant HSA domain II-like protein was lyophilized in the usual manner to obtain a lyophilized formulation.

Example 2

According to the procedures described in Japanese Laid-Open Patent Publication No. 2010-172277, HSA domain II gene (SEQ ID NO: 11) was obtained and integrated into the genome of *Pichia* yeast to produce cells expressing HSA domain II. After that, the yeast was cultured, and HSA domain II was expressed and purified. The purified HSA domain II was confirmed by SDS-PAGE. The resultant HSA domain II-like protein was a protein composed of the domain II, having the amino acid sequence of SEQ ID NO: 6 (positions 187 to 385 of SEQ ID NO: 10), and having a molecular weight of 22 kDa. The resultant HSA domain II-like protein was lyophilized in the usual manner to obtain a lyophilized formulation.

Experimental Example 1

The HSA domain II-like protein obtained in Example 1 (hereinafter, referred to as 20 kDa fragment) and HSA domain II-like protein obtained in Example 2 (hereinafter, also referred to as domain II) were examined for binding ability with respect to 4Z, 15Z-BR.

Figure 2:
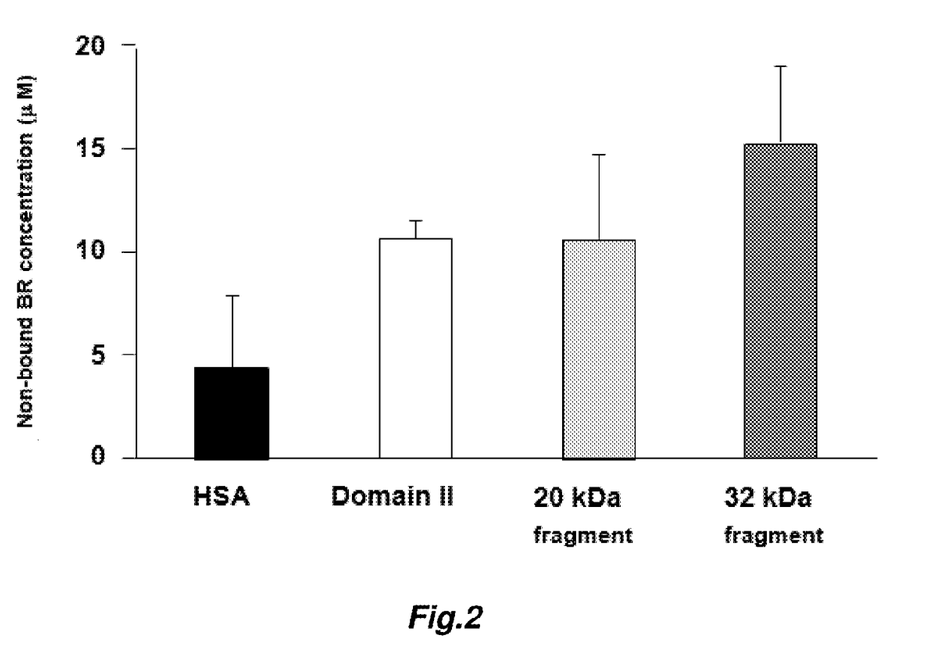
FIG. 2 is a graph showing the binding ability with respect to 4Z, 15Z-BR for serum albumin domain II-like proteins obtained in Example 1 and Example 2.

The concentration of free BR (4Z, 15Z-BR) was measured with improvement of the method of Brodersen (Brodersen et al. J Clin Invest 1974; 54: 1353-64). Two hundred microliters of a mixed solution of 60 μM BR and 30 μM protein was added to a 96 well immunoplate, and was allowed to stand for 20 minutes at 37° C. Ten microliters of 1.75 mM $H_2O_2$ was added thereto, and the mixture was allowed to stand for 3 minutes, and 10 μL of 1 μg/mL peroxidase (derived from horseradish) (Sigma) solution was then added to start the reaction. For 10 minutes after the addition, absorbance at 450 nm of each well was measured with an immunoplate reader. A calibration curve was created by plotting the initial oxidation rate and BR concentration, and the concentration of free BR was calculated. The results are shown in FIG. 2. The binding ability of 20 kDa fragment with respect to 4Z, 15Z-BR was equivalent to that of the domain II.

Experimental Example 2

Figure 3:
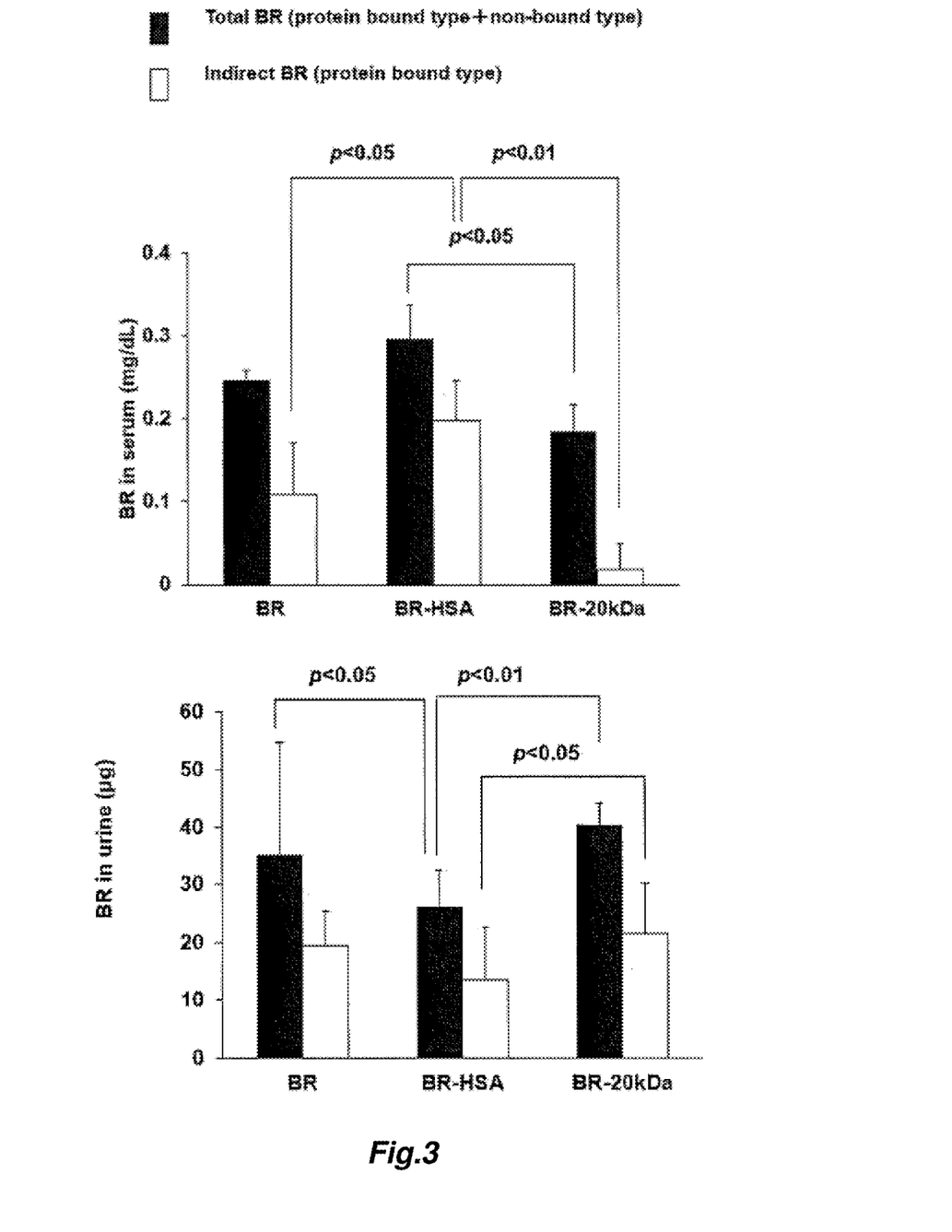
FIG. 3 is a graph showing the 4Z, 15Z-BR excretion enhancing effect of a human serum albumin domain II-like protein obtained in Example 1.
Figure 4:
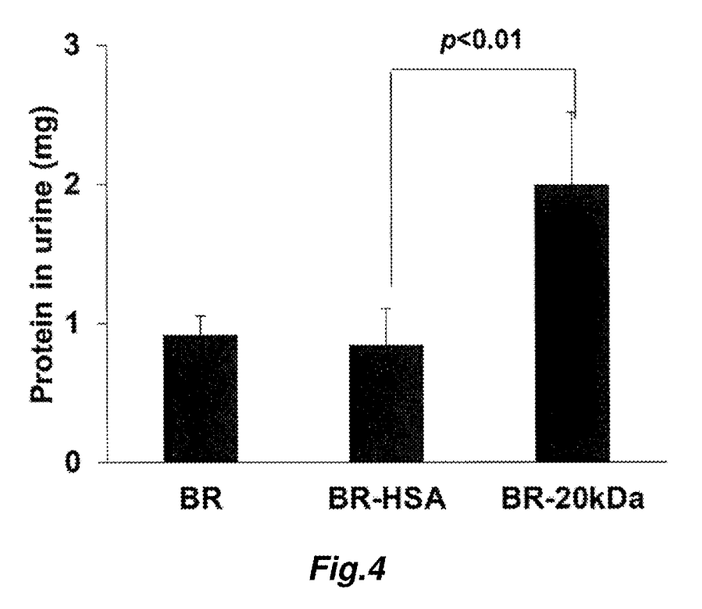
FIG. 4 is a graph showing the 4Z, 15Z-BR excretion enhancing effect of a human serum albumin domain II-like protein obtained in Example 1.

The 20 kDa fragment was examined on 4Z, 15Z-BR renal excretion enhancing effect. Rats were divided into three groups, each of which consisted of three rats. 4Z,15Z-BR (560 μg/bodyweight) was administered to the rats of the first group (BR group), 4Z,15Z-BR (560 μg/bodyweight) and HSA (62,800 μg/bodyweight) were administered to the rats of the second group (BR-HSA group), and 4Z,15Z-BR (560 μg/bodyweight) and the 20 kDa fragment (18,900 μg/bodyweight) were administered to the rats of the third group (BR-20 kDa group). After 2 hours, blood samples and urine samples were collected, and the concentration of 4Z, 15Z-BR in serum and the concentration of 4Z, 15Z-BR in 0.75-2.25 ml of urine were measured. The concentrations of BR in serum and in urine were measured using QuantiChrom™ Bilirubin Assay Kit (BioAssay Systems). The concentrations of total BR and indirect BR were measured according to the procedure of the kit. The results are shown in FIG. 3. The concentration of total 4Z, 15Z-BR in serum in the combined administration with the 20 kDa fragment was significantly lowered compared with the combined administration with HSA. Particularly, the concentration of protein bound type 4Z, 15Z-BR was remarkably lowered. The amount of total 4Z, 15Z-BR in urine in the combined administration with the 20 kDa fragment was significantly increased compared with the combined administration with HSA. Moreover, the amount of protein in urine was measured. The results are shown in FIG. 4. Protein in urine in the combined administration with the 20 kDa fragment was significantly increased compared with the combined administration with HSA. This shows that the 20 kDa fragment was bound to 4Z, 15Z-BR and excreted into urine.

INDUSTRIAL APPLICABILITY

Since the bilirubin excretion enhancer of the present invention binds to bilirubin in the body and is excreted out of the body, it is effective for the excretion and removal of bilirubin in the body, the treatment of hyperbilirubinemia, and so on.

The invention claimed is:

1. A method for enhancement of bilirubin excretion comprising administering a peptide consisting of the amino acid sequence of SEQ ID NO: 9 to a patient in need thereof.

2. A method according to claim 1, wherein the enhancement of bilirubin excretion is enhancement of urinary excretion.

3. A method according to claim 1, wherein the enhancement of bilirubin excretion is enhancement of 4Z, 15Z-bilirubin-IXα excretion.

* * * * *

SEQUENCE LISTING

<160> NUMBER OF SEQ ID NOS: 11

<210> SEQ ID NO 1
<211> LENGTH: 62

```
<212> TYPE: PRT
<213> ORGANISM: Homo sapiens

<400> SEQUENCE: 1

Asp Glu Gly Lys Ala Ser Ser Ala Lys Gln Arg Leu Lys Cys Ala Ser
1               5                   10                  15

Leu Gln Lys Phe Gly Glu Arg Ala Phe Lys Ala Trp Ala Val Ala Arg
            20                  25                  30

Leu Ser Gln Arg Phe Pro Lys Ala Glu Phe Ala Glu Val Ser Lys Leu
        35                  40                  45

Val Thr Asp Leu Thr Lys Val His Thr Glu Cys Cys His Gly
    50                  55                  60

<210> SEQ ID NO 2
<211> LENGTH: 109
<212> TYPE: PRT
<213> ORGANISM: Homo sapiens

<400> SEQUENCE: 2

Asp Glu Gly Lys Ala Ser Ser Ala Lys Gln Arg Leu Lys Cys Ala Ser
1               5                   10                  15

Leu Gln Lys Phe Gly Glu Arg Ala Phe Lys Ala Trp Ala Val Ala Arg
            20                  25                  30

Leu Ser Gln Arg Phe Pro Lys Ala Glu Phe Ala Glu Val Ser Lys Leu
        35                  40                  45

Val Thr Asp Leu Thr Lys Val His Thr Glu Cys Cys His Gly Asp Leu
    50                  55                  60

Leu Glu Cys Ala Asp Asp Arg Ala Asp Leu Ala Lys Tyr Ile Cys Glu
65                  70                  75                  80

Asn Gln Asp Ser Ile Ser Ser Lys Leu Lys Glu Cys Cys Glu Lys Pro
                85                  90                  95

Leu Leu Glu Lys Ser His Cys Ile Ala Glu Val Glu Asn
            100                 105

<210> SEQ ID NO 3
<211> LENGTH: 112
<212> TYPE: PRT
<213> ORGANISM: Homo sapiens

<400> SEQUENCE: 3

Asp Glu Gly Lys Ala Ser Ser Ala Lys Gln Arg Leu Lys Cys Ala Ser
1               5                   10                  15

Leu Gln Lys Phe Gly Glu Arg Ala Phe Lys Ala Trp Ala Val Ala Arg
            20                  25                  30

Leu Ser Gln Arg Phe Pro Lys Ala Glu Phe Ala Glu Val Ser Lys Leu
        35                  40                  45

Val Thr Asp Leu Thr Lys Val His Thr Glu Cys Cys His Gly Asp Leu
    50                  55                  60

Leu Glu Cys Ala Asp Asp Arg Ala Asp Leu Ala Lys Tyr Ile Cys Glu
65                  70                  75                  80

Asn Gln Asp Ser Ile Ser Ser Lys Leu Lys Glu Cys Cys Glu Lys Pro
                85                  90                  95

Leu Leu Glu Lys Ser His Cys Ile Ala Glu Val Glu Asn Asp Glu Met
            100                 105                 110

<210> SEQ ID NO 4
<211> LENGTH: 155
<212> TYPE: PRT
```

<213> ORGANISM: Homo sapiens

<400> SEQUENCE: 4

Asp Glu Gly Lys Ala Ser Ser Ala Lys Gln Arg Leu Lys Cys Ala Ser
1               5                   10                  15

Leu Gln Lys Phe Gly Glu Arg Ala Phe Lys Ala Trp Ala Val Ala Arg
            20                  25                  30

Leu Ser Gln Arg Phe Pro Lys Ala Glu Phe Ala Glu Val Ser Lys Leu
        35                  40                  45

Val Thr Asp Leu Thr Lys Val His Thr Glu Cys Cys His Gly Asp Leu
    50                  55                  60

Leu Glu Cys Ala Asp Asp Arg Ala Asp Leu Ala Lys Tyr Ile Cys Glu
65                  70                  75                  80

Asn Gln Asp Ser Ile Ser Ser Lys Leu Lys Glu Cys Cys Glu Lys Pro
                85                  90                  95

Leu Leu Glu Lys Ser His Cys Ile Ala Glu Val Glu Asn Asp Glu Met
            100                 105                 110

Pro Ala Asp Leu Pro Ser Leu Ala Ala Asp Phe Val Glu Ser Lys Asp
        115                 120                 125

Val Cys Lys Asn Tyr Ala Glu Ala Lys Asp Val Phe Leu Gly Met Phe
    130                 135                 140

Leu Tyr Glu Tyr Ala Arg Arg His Pro Asp Tyr
145                 150                 155

<210> SEQ ID NO 5
<211> LENGTH: 175
<212> TYPE: PRT
<213> ORGANISM: Homo sapiens

<400> SEQUENCE: 5

Asp Glu Gly Lys Ala Ser Ser Ala Lys Gln Arg Leu Lys Cys Ala Ser
1               5                   10                  15

Leu Gln Lys Phe Gly Glu Arg Ala Phe Lys Ala Trp Ala Val Ala Arg
            20                  25                  30

Leu Ser Gln Arg Phe Pro Lys Ala Glu Phe Ala Glu Val Ser Lys Leu
        35                  40                  45

Val Thr Asp Leu Thr Lys Val His Thr Glu Cys Cys His Gly Asp Leu
    50                  55                  60

Leu Glu Cys Ala Asp Asp Arg Ala Asp Leu Ala Lys Tyr Ile Cys Glu
65                  70                  75                  80

Asn Gln Asp Ser Ile Ser Ser Lys Leu Lys Glu Cys Cys Glu Lys Pro
                85                  90                  95

Leu Leu Glu Lys Ser His Cys Ile Ala Glu Val Glu Asn Asp Glu Met
            100                 105                 110

Pro Ala Asp Leu Pro Ser Leu Ala Ala Asp Phe Val Glu Ser Lys Asp
        115                 120                 125

Val Cys Lys Asn Tyr Ala Glu Ala Lys Asp Val Phe Leu Gly Met Phe
    130                 135                 140

Leu Tyr Glu Tyr Ala Arg Arg His Pro Asp Tyr Ser Val Val Leu Leu
145                 150                 155                 160

Leu Arg Leu Ala Lys Thr Tyr Glu Thr Thr Leu Glu Lys Cys Cys
                165                 170                 175

<210> SEQ ID NO 6
<211> LENGTH: 199
<212> TYPE: PRT

<213> ORGANISM: Homo sapiens

<400> SEQUENCE: 6

Asp Glu Gly Lys Ala Ser Ser Ala Lys Gln Arg Leu Lys Cys Ala Ser
1               5                   10                  15

Leu Gln Lys Phe Gly Glu Arg Ala Phe Lys Ala Trp Ala Val Ala Arg
                20                  25                  30

Leu Ser Gln Arg Phe Pro Lys Ala Glu Phe Ala Glu Val Ser Lys Leu
            35                  40                  45

Val Thr Asp Leu Thr Lys Val His Thr Glu Cys Cys His Gly Asp Leu
50                  55                  60

Leu Glu Cys Ala Asp Asp Arg Ala Asp Leu Ala Lys Tyr Ile Cys Glu
65                  70                  75                  80

Asn Gln Asp Ser Ile Ser Ser Lys Leu Lys Glu Cys Cys Glu Lys Pro
                85                  90                  95

Leu Leu Glu Lys Ser His Cys Ile Ala Glu Val Glu Asn Asp Glu Met
            100                 105                 110

Pro Ala Asp Leu Pro Ser Leu Ala Ala Asp Phe Val Glu Ser Lys Asp
        115                 120                 125

Val Cys Lys Asn Tyr Ala Glu Ala Lys Asp Val Phe Leu Gly Met Phe
130                 135                 140

Leu Tyr Glu Tyr Ala Arg Arg His Pro Asp Tyr Ser Val Val Leu Leu
145                 150                 155                 160

Leu Arg Leu Ala Lys Thr Tyr Glu Thr Thr Leu Glu Lys Cys Cys Ala
                165                 170                 175

Ala Ala Asp Pro His Glu Cys Tyr Ala Lys Val Phe Asp Glu Phe Lys
            180                 185                 190

Pro Leu Val Glu Glu Pro Gln
        195

<210> SEQ ID NO 7
<211> LENGTH: 112
<212> TYPE: PRT
<213> ORGANISM: Homo sapiens

<400> SEQUENCE: 7

Asp Glu Gly Lys Ala Ser Ser Ala Lys Gln Arg Leu Lys Cys Ala Ser
1               5                   10                  15

Leu Gln Lys Phe Gly Glu Arg Ala Phe Lys Ala Trp Ala Val Ala Arg
                20                  25                  30

Leu Ser Gln Arg Phe Pro Lys Ala Glu Phe Ala Glu Val Ser Lys Leu
            35                  40                  45

Val Thr Asp Leu Thr Lys Val His Thr Glu Cys Cys His Gly Asp Leu
50                  55                  60

Leu Glu Cys Ala Asp Asp Arg Ala Asp Leu Ala Lys Tyr Ile Cys Glu
65                  70                  75                  80

Asn Gln Asp Ser Ile Ser Ser Lys Leu Lys Glu Cys Cys Glu Lys Pro
                85                  90                  95

Leu Leu Glu Lys Ser His Cys Ile Ala Glu Val Glu Asn Asp Glu Met
            100                 105                 110

<210> SEQ ID NO 8
<211> LENGTH: 149
<212> TYPE: PRT
<213> ORGANISM: Homo sapiens

<400> SEQUENCE: 8

Tyr Ala Pro Glu Leu Leu Phe Phe Ala Lys Arg Tyr Lys Ala Phe
1               5                   10                  15

Thr Glu Cys Cys Gln Ala Ala Asp Lys Ala Ala Cys Leu Leu Pro Lys
            20                  25                  30

Leu Asp Glu Leu Arg Asp Glu Gly Lys Ala Ser Ser Ala Lys Gln Arg
            35                  40                  45

Leu Lys Cys Ala Ser Leu Gln Lys Phe Gly Glu Arg Ala Phe Lys Ala
50                  55                  60

Trp Ala Val Ala Arg Leu Ser Gln Arg Phe Pro Lys Ala Glu Phe Ala
65                  70                  75                  80

Glu Val Ser Lys Leu Val Thr Asp Leu Thr Lys Val His Thr Glu Cys
                85                  90                  95

Cys His Gly Asp Leu Leu Glu Cys Ala Asp Asp Arg Ala Asp Leu Ala
            100                 105                 110

Lys Tyr Ile Cys Glu Asn Gln Asp Ser Ile Ser Ser Lys Leu Lys Glu
            115                 120                 125

Cys Cys Glu Lys Pro Leu Leu Glu Lys Ser His Cys Ile Ala Glu Val
130                 135                 140

Glu Asn Asp Glu Met
145

<210> SEQ ID NO 9
<211> LENGTH: 175
<212> TYPE: PRT
<213> ORGANISM: Homo sapiens

<400> SEQUENCE: 9

Cys Thr Ala Phe His Asp Asn Glu Glu Thr Phe Leu Lys Lys Tyr Leu
1               5                   10                  15

Tyr Glu Ile Ala Arg Arg His Pro Tyr Phe Tyr Ala Pro Glu Leu Leu
            20                  25                  30

Phe Phe Ala Lys Arg Tyr Lys Ala Ala Phe Thr Glu Cys Cys Gln Ala
            35                  40                  45

Ala Asp Lys Ala Ala Cys Leu Leu Pro Lys Leu Asp Glu Leu Arg Asp
50                  55                  60

Glu Gly Lys Ala Ser Ser Ala Lys Gln Arg Leu Lys Cys Ala Ser Leu
65                  70                  75                  80

Gln Lys Phe Gly Glu Arg Ala Phe Lys Ala Trp Ala Val Ala Arg Leu
                85                  90                  95

Ser Gln Arg Phe Pro Lys Ala Glu Phe Ala Glu Val Ser Lys Leu Val
            100                 105                 110

Thr Asp Leu Thr Lys Val His Thr Glu Cys Cys His Gly Asp Leu Leu
            115                 120                 125

Glu Cys Ala Asp Asp Arg Ala Asp Leu Ala Lys Tyr Ile Cys Glu Asn
130                 135                 140

Gln Asp Ser Ile Ser Ser Lys Leu Lys Glu Cys Cys Glu Lys Pro Leu
145                 150                 155                 160

Leu Glu Lys Ser His Cys Ile Ala Glu Val Glu Asn Asp Glu Met
                165                 170                 175

<210> SEQ ID NO 10
<211> LENGTH: 585
<212> TYPE: PRT
<213> ORGANISM: Homo sapiens

<400> SEQUENCE: 10

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415
```

```
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 11
<211> LENGTH: 597
<212> TYPE: DNA
<213> ORGANISM: Homo sapiens

<400> SEQUENCE: 11
gatgaaggga aggcttcgtc tgccaaacag agactcaagt gtgccagtct ccaaaaattt      60
ggagaaagag ctttcaaagc atgggcagta gctcgcctga ccagagatt tcccaaagct     120 gagtttgcag aagtttccaa gttagtgaca gatcttacca aagtccacac ggaatgctgc    180
catggagatc tgcttgaatg tgctgatgac agggcggacc ttgccaagta tatctgtgaa    240
aatcaagatt cgatctccag taaactgaag gaatgctgtg aaaaacctct gttggaaaaa    300
tcccactgca ttgccgaagt ggaaaatgat gagatgcctg ctgacttgcc ttcattagct    360
gctgattttg ttgaaagtaa ggatgttttgc aaaaactatg ctgaggcaaa ggatgtcttc    420
ctgggcatgt ttttgtatga atatgcaaga aggcatcctg attactctgt cgtgctgctg    480
ctgagacttg ccaagacata tgaaaccact ctagagaagt gctgtgccgc tgcagatcct    540
catgaatgct atgccaaagt gttcgatgaa tttaaacctc ttgtggaaga gcctcag       597
```